(12) United States Patent
McGrath

(10) Patent No.: US 11,717,072 B2
(45) Date of Patent: *Aug. 8, 2023

(54) LIPSTICK ARRANGEMENT

(71) Applicant: Pat McGrath Cosmetics LLC, New York, NY (US)

(72) Inventor: Patricia McGrath, New York, NY (US)

(73) Assignee: Pat McGrath Cosmetics LLC, New York, NY (US)

( * ) Notice: Subject to any disclaimer, the term of this patent is extended or adjusted under 35 U.S.C. 154(b) by 13 days.

This patent is subject to a terminal disclaimer.

(21) Appl. No.: 17/112,957

(22) Filed: Dec. 4, 2020

(65) Prior Publication Data

US 2021/0204673 A1  Jul. 8, 2021

Related U.S. Application Data

(63) Continuation-in-part of application No. 16/747,800, filed on Jan. 21, 2020, now Pat. No. 10,863,814, (Continued)

(51) Int. Cl.
*A45D 40/06* (2006.01)
*A45D 40/00* (2006.01)
*A61Q 1/06* (2006.01)

(52) U.S. Cl.
CPC ............... *A45D 40/06* (2013.01); *A61Q 1/06* (2013.01); *A45D 2040/0012* (2013.01); *A45D 2040/0025* (2013.01); *A61K 2800/43* (2013.01)

(58) Field of Classification Search
CPC .. A45D 2040/0012; A45D 40/06; A61Q 1/06; A61K 8/0229; A61K 8/55
See application file for complete search history.

(56) References Cited

U.S. PATENT DOCUMENTS 2,032,669 A * 3/1936 Seaver .................. A45D 40/06
                                                  401/71
2,093,685 A   9/1937 Morrison
(Continued)

FOREIGN PATENT DOCUMENTS

EP    2543276 A1    1/2013
GB    645143 A    10/1950
(Continued)

OTHER PUBLICATIONS

KR200397589Y1_MT; machine translation of KR200397589Y1 by espacenet obtaintained on Feb. 25, 2022.*
(Continued)

*Primary Examiner* — David J Walczak
(74) *Attorney, Agent, or Firm* — Ziegler IP Law Group

(57) ABSTRACT

A lipstick arrangement including a casing and a protective covering. The casing includes a first part including a carrier at a bottom region, a second part and a protruding element attached to the second part. Lipstick bullet is mounted on the carrier and has an elongate shape including a sloping top portion. The carrier is operatively coupled to the first part and the second part and the carrier is arranged to move in an axial direction relative to the second part in response to the first part being rotated relative to the second part. The protective covering covers the first part of the casing when applied to the casing. The sloping top portion of the lipstick bullet is configured to face away from the protruding element when the lipstick bullet is unscrewed to a fully deployed position.

14 Claims, 9 Drawing Sheets

Related U.S. Application Data which is a continuation of application No. 16/032,619, filed on Jul. 11, 2018, now Pat. No. 10,548,385.

(56) References Cited

U.S. PATENT DOCUMENTS

| | | | |
|---|---|---|---|
| 2,099,488 A * | 11/1937 | Kasdan | A45D 40/06 401/86 |
| 2,108,512 A | 2/1938 | Reichenbach | |
| 2,143,155 A * | 1/1939 | Kasdan | A45D 40/06 401/71 |
| D124,652 S | 1/1941 | Kane | |
| 2,238,368 A * | 4/1941 | Parkin | A45D 40/06 401/86 |
| 2,273,138 A | 2/1942 | Peterson | |
| 2,302,459 A * | 11/1942 | Noel | A45D 40/06 401/78 |
| D135,799 S | 6/1943 | Richter | |
| 2,349,799 A | 5/1944 | Lee | |
| 2,367,992 A | 1/1945 | Berls | |
| 2,395,535 A * | 2/1946 | Crane | A45D 40/06 401/79 |
| 2,419,526 A * | 4/1947 | Anderson | A45D 40/06 401/86 |
| 2,458,020 A | 1/1949 | Olsen | |
| 2,504,490 A * | 4/1950 | Felstiner | A45D 40/06 401/78 |
| 2,510,422 A * | 6/1950 | Seaver | A45D 40/06 401/86 |
| 2,511,966 A * | 6/1950 | Felstiner | A45D 40/06 401/61 |
| 2,512,476 A | 6/1950 | Birnkrant et al. | |
| 2,514,969 A * | 7/1950 | Politzer | A45D 40/065 401/59 |
| 2,521,169 A * | 9/1950 | Houlihan | A45D 40/12 401/61 |
| 2,565,346 A | 8/1951 | Braselton | |
| 2,609,093 A | 9/1952 | Lynn | |
| 2,776,051 A | 1/1957 | Warren, Jr. | |
| 2,921,675 A * | 1/1960 | Clark | A45D 40/06 401/98 |
| 2,951,584 A | 9/1960 | Bauer | |
| 2,990,054 A | 6/1961 | Gellman | |
| 3,002,611 A * | 10/1961 | Doblin | A45D 40/06 401/86 |
| 3,152,691 A * | 10/1964 | Hultgren | A45D 40/06 401/61 |
| 3,175,853 A * | 3/1965 | Gilbertson | B65D 50/046 220/8 |
| 3,317,036 A | 5/1967 | Cherba | |
| 3,380,795 A | 4/1968 | Gruska | |
| 3,438,714 A * | 4/1969 | Seaver | A45D 40/06 401/74 |
| 3,531,212 A * | 9/1970 | Landen | A45D 40/06 401/75 |
| 3,539,266 A | 11/1970 | Hultgren | |
| 3,789,857 A | 2/1974 | Ikeda et al. | |
| 4,422,545 A * | 12/1983 | Kadoory | A45D 40/06 401/98 |
| D280,140 S | 8/1985 | Bakic | |
| 4,579,134 A | 4/1986 | Moore | |
| D298,472 S | 11/1988 | Simonetti | |
| 4,792,251 A | 12/1988 | Ryder | |
| D301,772 S | 6/1989 | McCready | |
| D303,301 S | 9/1989 | McCready | |
| D307,953 S | 5/1990 | McCready | |
| D315,969 S | 4/1991 | McCready | |
| D317,664 S | 6/1991 | Bakic | |
| D333,885 S | 3/1993 | Laing | |
| D343,028 S | 1/1994 | Chen | |
| D365,176 S | 12/1995 | Heinrich | |
| D368,555 S | 4/1996 | Wacker | |
| 5,738,067 A | 4/1998 | Landwehr et al. | |
| 5,842,803 A * | 12/1998 | Furnell | A45D 40/12 401/78 |
| D410,570 S | 6/1999 | Lerolle | |
| D416,355 S * | 11/1999 | Lerolle | D28/7 |
| 6,109,807 A | 8/2000 | Joulia et al. | |
| 6,200,047 B1 | 3/2001 | Holloway | |
| D441,145 S | 4/2001 | Chang | |
| 6,340,258 B2 | 1/2002 | Gueret | |
| D468,869 S | 1/2003 | Thorpe et al. | |
| D505,519 S | 5/2005 | Korba | |
| 7,112,002 B2 | 9/2006 | Susini et al. | |
| 7,293,926 B2 * | 11/2007 | Gueret | A45D 40/10 401/74 |
| 7,553,101 B2 | 6/2009 | Harano et al. | |
| 8,083,427 B2 * | 12/2011 | Maddy | A45D 40/00 401/98 |
| 8,328,445 B2 | 12/2012 | Martins et al. | |
| 8,985,881 B2 | 3/2015 | Hefetz et al. | |
| D785,871 S | 5/2017 | Staab et al. | |
| D794,247 S * | 8/2017 | Xavier | D28/4 |
| 10,028,567 B2 | 7/2018 | Lee et al. | |
| D906,594 S * | 12/2020 | McGrath | D28/89 |
| D929,659 S * | 8/2021 | Otani | D28/85 |
| 11,076,679 B1 * | 8/2021 | Chung | A45D 40/04 |
| D933,899 S * | 10/2021 | Yang | D28/77 |
| 11,140,965 B2 * | 10/2021 | Lee | A45D 40/00 |
| D944,458 S * | 2/2022 | Otani | D28/85 |
| D946,831 S * | 3/2022 | McGrath | D28/89 |
| 2004/0253036 A1 | 12/2004 | Habatjou | |
| 2007/0217857 A1 | 9/2007 | Ho | |
| 2008/0152418 A1 | 6/2008 | Maddy | |
| 2010/0290827 A1 | 11/2010 | Komatsuda et al. | |
| 2013/0022384 A1 | 1/2013 | Yan | |
| 2013/0343800 A1 | 12/2013 | Drugeon et al. | |
| 2015/0208785 A1 | 7/2015 | Holloway | |
| 2016/0249729 A1 | 9/2016 | Hermouet et al. | |
| 2018/0352935 A1 | 12/2018 | Lin | |
| 2019/0183230 A1 * | 6/2019 | Denece | A45D 40/18 |
| 2020/0015570 A1 | 1/2020 | McGrath | |
| 2020/0337439 A1 * | 10/2020 | Yoshimura | A45D 40/02 |
| 2021/0076801 A1 * | 3/2021 | Liu | A45D 40/06 |
| 2021/0112946 A1 * | 4/2021 | Kim | A45D 40/04 |
| 2021/0298452 A1 * | 9/2021 | Chung | A45D 40/026 |
| 2021/0298454 A1 * | 9/2021 | Lecureuil | A45D 40/16 |
| 2021/0321746 A1 * | 10/2021 | Jourdain | A45D 40/06 |
| 2022/0031045 A1 * | 2/2022 | Trochel | A45D 40/06 |

FOREIGN PATENT DOCUMENTS

| | | | |
|---|---|---|---|
| KR | 200397589 Y1 * | 10/2005 | |
| KR | 200397589 Y1 | 10/2005 | |
| WO | 2018/037170 A1 | 3/2018 | |

OTHER PUBLICATIONS

Lip Definition & Meaning—Merriam-Webster; obtained on Feb. 26, 2022 from: https://www.merriam-webster.com/dictionary/lip.*

Ajumker, "Natural Lip Balm Color Changing Jelly Lipstick Natural Moisturizing Temptation Dried flower lip balm Colorless Lip Balm Anti-wrinkle Repair Female Winter Lip Balm Green", Retrieved on Apr. 21, 2021, available at the URL: https://www.amazon.co.uk/AJUMKER-Moisturizing-Temptation-Colorless-Anti-wrinkle/dp/B07X87DT5T/ref=pd, 7 pages.

"Charlotte Tilbury Hot Lips 2 | Lipstick Swatches and Review", Youtube Video, Retrieved on Apr. 21, 2021, available at the URL: https://www.youtube.com/watch?v=IAZJsD6qgR0, 3 pages.

Intellectual Property Office, Search Report under Section 17(5), Application No. GB2000367.9, dated Jul. 1, 2020, 5 pages.

International Search Report and Written Opinion of The International Searching authority, Application No. PCT/IB2021/050130, dated Apr. 1, 2021, 12 pages.

"Lipstick Case", Pinterest, Retrieved on Apr. 21, 2021, available at the URL: https://www.pinterest.co.uk/pin/423056958728914248/, 6 pages.

"Signature Lipstick in Vintage Mauve", Retrieved on Apr. 21, 2021, available at the URL: https://www.makeupalley.com/product/showreview.asp?ItemId=137667/Signature-Lipstick-in-Vintage-Mauve/Estee-Lauder/Lipstick, 3 pages.

(56) References Cited

OTHER PUBLICATIONS

"vintage lipstick", Google Search, Retrieved on Apr. 21, 2021, available at the URL: https://www.google.com/search?safe=strict&rlz=1C5CHFA_enGB939&sxsrf=ALeKk02ZQfik2JUvBfbteFiR8QE7R9gVzQ:1618481697766&source=univ&tbm=isch&q=vintage +lipstick&sa=X&ved=2ahUKEwiSsq6VgoDwAhVPUBUIHXUcCG0QjJkEegQIDRAB&biw=1438&bih=593, 3 pages.

"Vintage Lipstick at the Makeup Museum in New York City", Wikipedia, Retrieved on Apr. 21, 2021, available at the URL: https://en.wikipedia.org/wiki/File:Vintage_Lipstick_at_the_Makeup_Museum_in_New_York_City.jpg, 3 pages.

"Vintage lipstick collection", Pinterest, Retrieved on Apr. 21, 2021, available at URL: https://www.pinterest.com.au/pin/361484307585343438/, 3 pages.

"Vintage lipstick tubes were so pretty!", reddit.com, Retrieved on Apr. 21, 2021 at URL: https://www.reddit.com/r/MakeupAddiction/comments/14twj3/vintage_lipstick_tubes_were_so_pretty/, 20 pages.

"YSL Rouge Volupté Shine Lipstick", Boots, Retrieved on Apr. 21, 2021, available at the URL: https://www.boots.com/yves-saint-laurent-rouge-volupte-shine-lipstick?cm, 8 pages.

"Salvador Dali Perfume & Cologne", Pinterest, Apr. 2021, available at the URL: https://www.pinterest.com/pin/300615343858059034/, 9 pages.

\* cited by examiner

LIPSTICK ARRANGEMENT

TECHNICAL FIELD

The present disclosure relates generally to cosmetic applicators; and more specifically, to a lipstick arrangement.

BACKGROUND

Humans often desire to appear presentable, and therefore groom and style themselves in an attempt to appear beautiful. Cosmetics and other beauty products are often employed for such grooming and styling purposes. Such beauty products include mascara, kohl, lip balm, lipstick and so forth; the beauty products enable facial defining features that are regarded as being aesthetically attractive to be visually emphasized. The beauty products, for example lipstick and lip balm, often come in a form of a pallet, a crayon, a bullet and the like. When the lip balms and lipsticks are provided in a form of a lipstick bullet, they are often provided in a casing that stores the lipstick bullet; the lipstick bullet can be progressively deployed for use or retracted for storage by employing a screw mechanism, wherein the screw mechanism is screwed or unscrewed by a given user while using the lipstick bullet. Such casings including lipstick bullets are contemporarily widely used on account of their practicality and portability.

A known contemporary lipstick arrangement comprises a casing for storing a lipstick bullet, wherein the lipstick bullet has a soft wax-like and oily consistency that enables thin layer of a few micrometers to be deposited on a tissue surface, for example lips, by swiping a distal end of the lipstick bullet in contact with the tissue surface. The casing has a top portion and a bottom portion that are rotatably coupled together, wherein the top portion is designed to hold and protect the lipstick bullet. Moreover, in operation, the top portion can be rotated relative to the bottom portion to deploy or retract the lipstick bullet, when the casing is in use. Often, for aesthetic reasons, the top and bottom portions of the casing have exterior surfaces that are lustrous and smooth, thereby imparting an attractive appearance to the casing.

However, such lustrous and smooth exterior surfaces of the top and bottom portions of the casing are disadvantageous in that any smear of lipstick from the lipstick bullet onto the exterior surfaces makes them slippery and uncomfortable to hold. Therefore, the casing often does not provide a user-friendly approach for applying lipstick or lip balm by way of gripping the top portion or the bottom portion, or both, of the casing.

As aforementioned, the casing has a smooth and slippery exterior surfaces of the top and bottom portion which makes it difficult for a given user to hold the casing, for example on account of a lack of grip, when applying the lipstick, for example, in a situation where there are smeared traces of make up or moisture on hands of the given user holding the casing.

Therefore, there exists a need for a more practical lipstick arrangement that is capable to addressing the aforementioned technical drawbacks associated with known types of lipstick arrangements.

SUMMARY

The present disclosure seeks to provide an improved lipstick arrangement. Moreover, the present disclosure seeks to provide at least partial solution to existing technical problem of discomfort when applying lipsticks. An aim of the present disclosure is to provide solution that at least partially overcomes the problems encountered in known art.

In one aspect, an embodiment of the present disclosure provides a lipstick arrangement comprising:
   a casing comprising:
      a first part including a carrier at a bottom region, wherein a lipstick bullet is mounted on the carrier and has an elongate shape comprising a sloping top portion;
      a second part, wherein the carrier is operatively coupled to the first part and the second part, and wherein the carrier is arranged to move in an axial direction relative to the second part in response to the first part being rotated relative to the second part; and
      a protruding element attached to the second part; and
   a protective covering that is configured to cover the first part of the casing when applied to the casing,
wherein the sloping top portion of the lipstick bullet is configured to face away from the protruding element when the lipstick bullet is unscrewed to a fully deployed position.

Embodiments of the present disclosure substantially eliminate or at least partially address the aforementioned problems in the prior art and allow for an efficient and comfortable lipstick arrangement. The present disclosure provides for a better grip that enables a user to hold the lipstick arrangement efficiently and allows for movement of fingers of the user without slipping.

Optionally, sloping top portion of the lipstick bullet is configured to face in a radial direction that is in a range of 60 degrees to 180 degrees away from radial direction of the protruding element.

Optionally, the lipstick arrangement is implemented such that the sloping top portion of the lipstick bullet is configured to face in a radial direction that is mutually opposite to a radial direction of the protruding element Optionally, the lipstick arrangement is implemented such that the lipstick bullet comprises a ridge configured to face in the same direction as the protruding element.

More optionally, the lipstick arrangement is implemented such that the ridge extends from 10% to 80% of an elongate length of the lipstick bullet.

Optionally, the lipstick arrangement is implemented such that the protective covering comprises internal facets for abutting onto the first part of the casing.

Optionally, the lipstick arrangement is implemented such that the lipstick arrangement comprises a grip-enhancing coating having an anti-slip texture on the casing and the protective covering, that is configured to provide a better grip to fingers of a user holding the lipstick arrangement.

Optionally, the lipstick arrangement is implemented such that the protruding element is any one of: a lip structure, a crown structure, a heart structure, a diamond structure, or a combination thereof.

Optionally, the protruding element is configured on the lipstick arrangement in a slanted or an upright orientation.

Optionally, the lipstick arrangement is implemented such that the protruding element positions in operation the lipstick arrangement in the packaging carton in a way that prevents damage to the packaging during transport or when stored in a purse, a bag, and a backpack.

Optionally, the lipstick arrangement is implemented such that the lipstick bullet mounted on the carrier is actuated along an elongate axis of the lipstick arrangement, in response to the first part being rotated relative to the second part, for deploying and retracting the lipstick bullet from the casing.

Optionally, the lipstick arrangement is implemented such that the lipstick bullet is a cosmetic composition comprising at least one of the following ingredients: a non-ionic alkyl phosphate; a base; a humectant; a water; a structuring agent; an oil; a pigment; a glitter.

Optionally, the lipstick arrangement is implemented such that the protective covering is arranged to be snap-fit retained onto the protruding element, when the protective covering is applied to cover the first part.

According to a second aspect, there is a provided a lipstick bullet when used in the lipstick arrangement of the first aspect, wherein the lipstick bullet is a lip color, lip balm, or lip gloss.

Optionally, the lipstick bullet gives a glossy, lustrous, matte, shimmery effect, when applied to lips of a given user.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
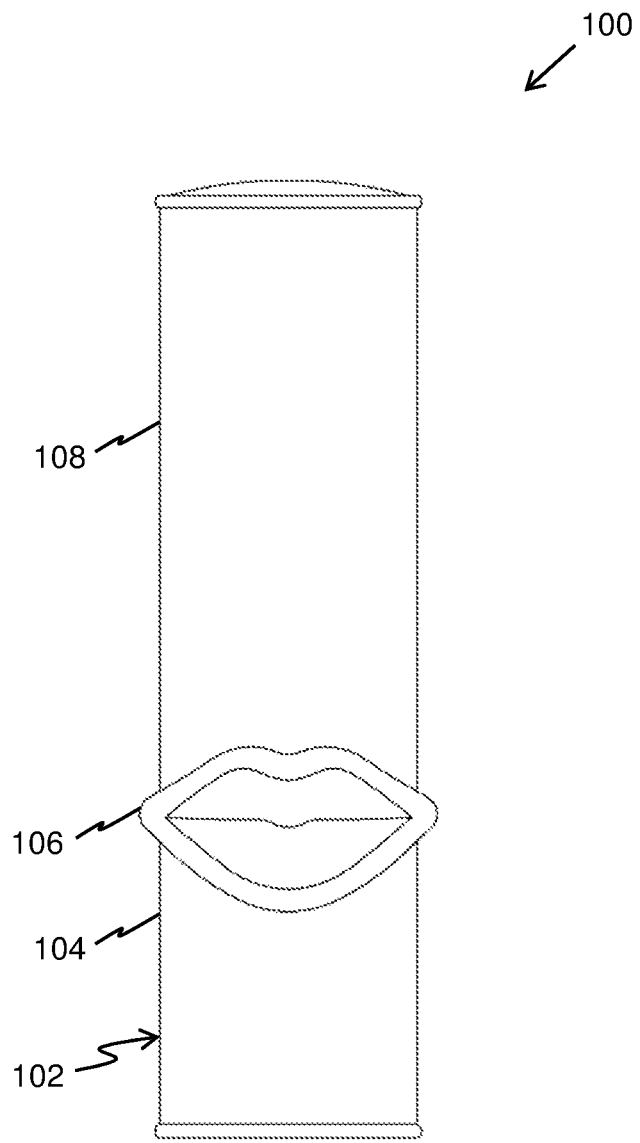
FIG. 1 is an illustration of a front view of a lipstick arrangement in a closed configuration, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, there is provided a lipstick arrangement comprising:
  a casing comprising:
    a first part including a carrier at a bottom region, wherein a lipstick bullet is mounted on the carrier and has an elongate shape comprising a sloping top portion;
    a second part, wherein the carrier is operatively coupled to the first part and the second part, and wherein the carrier is arranged to move in an axial direction relative to the second part in response to the first part being rotated relative to the second part; and
    a protruding element attached to the second part; and
  a protective covering that is configured to cover the first part of the casing when applied to the casing,
wherein the sloping top portion of the lipstick bullet is configured to face away from the protruding element when the lipstick bullet is unscrewed to a fully deployed position.

The present disclosure provides a lipstick arrangement that stores a lipstick bullet, and that provides for an efficient application of the lipstick bullet when forming a film of lipstick onto lips. The lipstick arrangement disclosed herein provides in operation for an improved grip for a given user when holding the lipstick arrangement. Moreover, the grip provided by the lipstick arrangement increases comfort of the given user when holding and using the lipstick arrangement. A protruding element on the lipstick arrangement assists to reduce or prevent slipping of fingers of the given user while holding the lipstick arrangement. Moreover, a presence of the protruding element on one side of the lipstick arrangement provides for an ample amount of space for accommodating movement of fingers of the given user, when the given user is holding the lipstick arrangement. Furthermore, different angular orientations of protruding element and a sloping top portion of the lipstick bullet provides the given user with an indication for more optimal use of the lipstick arrangement. Hence, there is thereby prevented the lipstick bullet inside the lipstick arrangement from becoming damaged by an inappropriate manner of application of the lipstick bullet. Moreover, the different opposite angular orientations of the protruding element and the sloping top portion of the lipstick bullet allows for an easier and more efficient use of the lipstick arrangement in a situation that the given user has, for example, impaired eyesight.

Throughout the present disclosure, the term "lipstick arrangement" refers to a mechanical arrangement that, when in operation, stores a lipstick bullet. The lipstick arrangement of the present disclosure reduces a tendency for the lipstick bullet to break in a middle region thereof, and from becoming damaged. Furthermore, the lipstick arrangement provides a screw mechanism that allows user deployment and retraction of the lipstick bullet stored in the lipstick arrangement. Additionally, the lipstick arrangement ensures that the lipstick bullet becomes completely retracted before the lipstick arrangement is closed by attaching its protective covering for covering the lipstick bullet; the protective covering protects the lipstick bullet from dust, contaminants and other physical damage.

Throughout the present disclosure the term "lipstick bullet" refers to an elongate bar, stick and the like, wherein a distal end of the elongate bar, stick and the like is tapered, providing a shape that superficially resembles an ammunition bullet. Optionally, the lipstick bullet is manufactured to have a color akin to a lip color, a lip balm, a lip gloss and the like. More optionally, the lipstick bullet provides, when applied to the given user's lips, a glossy, lustrous, matte, shimmery and the like visual effect. In an example, the lipstick bullet may have included therein at least one of an added tint, a glitter, a fragrance. The lipstick bullet may have an angled, sloped portion on the distal end thereof, that provides a better interface for applying color or balm at corners and sides of lips of the given user. In an example embodiment, the lipstick bullet may have its distal end terminating in a pointed region. In another example, the lipstick bullet may have a blunt top, for example a truncated top. The lipstick bullet may comprise one or more of a non-ionic alkyl phosphate, a base, a humectant, water, a structuring agent, an oil, a pigment, and a glitter.

Optionally, the lipstick bullet has an odorless (namely, fragrance-free) formula and feels lightweight when applied by the given user to the given user's lips. Additionally, the lipstick bullet provides coverage on a desired area of the given user's lips in a single swipe application of the lipstick. Moreover, the lipstick bullet when applied to lips of the given user has a hydrating and moisturized benefit to the given user's lips. Moreover, the lipstick bullet has a formula with sun protection and vitamins. The lipstick bullet when applied to the given user's lips provides a satin finish, and provides for creamy gliding when swiping along the given user's lips.

Optionally, the lipstick bullet is a cosmetic composition comprising at least one of following ingredients: a non-ionic alkyl phosphate; a base; a humectant; a water; a structuring agent; an oil; a pigment; a glitter. Additionally, the cosmetic composition also optionally contains beeswax, ozocerite and candelilla wax. Furthermore, various oils and fats such as at least one of olive oil, mineral oil, cocoa butter, lanolin, petroleum and so forth are included in the lipstick bullet. The constituents of the lipstick bullet provide it with an attractive and long-lasting texture when applied on a given tissue area, for example onto the given user's lips. The constituents of the lipstick bullet also provide biological nourishment to the given tissue area.

It will be appreciated that a formula, texture, property associated with the lipstick bullet is only elucidated in the foregoing for a sake of clarity and is not to be constructed as limiting a variation of implementation of the lipstick bullet.

As aforementioned, the lipstick arrangement comprises the casing, wherein the casing provides in operation a screw mechanism for deploying and retracting the lipstick bullet. Optionally, the casing is manufactured from at least one of a fiber material, a plastics material, a metal or metal alloy, a combination of these or any element that can be used to achieve functioning of the casing. The casing includes following components: a first part, a second part and a protruding element, wherein the components are mutually coupled together in operation.

The first part comprises the carrier at the bottom region, wherein the lipstick bullet is mounted on the carrier. The first part has an elongate shape comprising a sloping top portion. The first part is a hollow elongate component having a central elongate axis and having a geometrical shape in cross-section (namely, in a plane that is orthogonal to the elongate central elongate axis) such as circular, polygonal, rectangular and the like that circumferentially includes the lipstick bullet. The first part is, for example, tubular in structure. In an example embodiment, when the lipstick bullet is completely unscrewed, the lipstick bullet becomes completely deployed and is spatially exposed from the first part of the casing. The first part is rotatable relative to the second part, about the aforesaid elongate axis that allows for screwing and unscrewing of the lipstick bullet. Beneficially, the first part is rotatable in a clockwise or an anti-clockwise direction relative to the second part. Moreover, the first part includes the carrier at a bottom region thereof that supports the lipstick bullet within the casing. The bottom region of the carrier may be flat, shallow or dome-shaped in structure. The carrier may have an exposed smooth surface. Alternatively, the carrier may have holes there in a random or deterministic pattern. The carrier is associated with the first part in a way that an upward and downward movement of the lipstick bullet is provided when the first part is rotated about the aforementioned elongate axis. The first part is mounted above the second part, when the lipstick arrangement is held in a vertically upright orientation.

Optionally, the lipstick bullet within the casing is replaced by removing a first lipstick bullet from the carrier and putting a second lipstick bullet in the carrier; this allows for the lipstick arrangement to recharged or recycled, therefore reducing environmental waste.

Furthermore, the lipstick arrangement comprises the second part. The second part is positioned below the first part of the lipstick arrangement, when the lipstick arrangement is deployed in a vertically upright orientation. In an example, the first part and the second part may have a circular cross-section, in a plane orthogonal to the aforesaid elongate axis. In another example, the first part may have a circular cross-section and the second part may have a rectangular cross-section.

As mentioned previously, the first part and the second part are configured to be mutually rotatable, wherein the carrier is operatively coupled to the first part and the second part. The carrier may be operatively coupled by a screw mechanism to the first part and the second part. The carrier is arranged to move in an axial direction relative to the second part in response to the first part being rotated relative to the second part. The screw mechanism enables movement of the lipstick carrier while screwing or unscrewing the lipstick bullet. Furthermore, the lipstick bullet can be screwed and unscrewed by rotating the first part relative to the second part.

Optionally, in operation, the first part is rotated in a clockwise direction and the second part is rotated in an anti-clockwise direction for retracting or deploying the lipstick bullet. Alternatively, the first part is rotated in an anti-clockwise direction and the second part is rotated in clockwise direction for retracting or deploying the lipstick bullet.

Optionally, the first part and/or the second part can be rotated, pressed or twisted or pulled to move the carrier in an axially upward direction to deploy the lipstick bullet for use. Moreover, the first part and/or the second part can be rotated, pressed or twisted or pulled to move the carrier in axially downward direction to retract the lipstick bullet back in the first part.

Furthermore, the lipstick arrangement comprises the protruding element attached to the second part. Optionally, the protruding element is attached at a top region of the second part. In an example, the protruding element may be deployed approximately in a middle region along the lipstick arrangement. In another example, the protruding element may be deployed approximately in the middle region of the first part of the lipstick arrangement. In yet another example, the protruding element may be deployed approximately in the middle region of the second part. The protruding element is a geometric or non-geometric structure that provides a grip for the given user to the second part of the lipstick arrangement. Beneficially, the protruding element provides a better grasp for the given user to hold the lipstick arrangement and allow for movement of the given user's fingers when holding the lipstick arrangement in operation. In an example, the protruding element may be a part of the second part. In another example, the protruding element may be a separate component attached to the second part. Furthermore, the protruding element is optionally manufactured from materials like plastics materials, fiber materials, metal or metal alloy, glass and the like.

Optionally, the protruding element is pushed or clicked for screwing or unscrewing the lipstick bullet. Additionally, the protruding element is rotated or pulled for screwing or unscrewing the lipstick bullet.

Optionally, the protruding element comprises a mechanism that functions as an opening button for the protective covering; for example, the protruding element provides for flexural retention over an outwardly projecting feature of the protective covering, so that the lipstick arrangement provides for "snap-fit" retention of the protective cover onto the protruding element. The protruding element is optionally pushed, pulled, rotated or moved in order to remove the protective covering from top of the casing. The protruding element in operation is susceptible to being manipulated to uncover the top of the casing, so that the lipstick bullet becomes deployed for swipe application to the given user's lips.

Optionally, the casing of the lipstick arrangement has a rough (for example, sand paper like) texture that provides for a better grip for the given user when holding the casing. Such a sand paper like texture potentially provides an attractive appearance to the lipstick arrangement. Additionally, the sand paper like texture substantially reduces a chance of slipping of fingers of the given user when holding the casing.

Optionally, the protruding element is any one of: a lip-shaped structure, a crown structure, a heart structure, a diamond structure, or a combination thereof. The protruding element beneficially imparts an aesthetic appeal to the lipstick arrangement. In an example, the protruding element is the crown structure made of shiny golden metal. In another example, the protruding element is the heart structure with shiny crystals around it. In such example, the heart structure may be a crooked heart structure. In yet another example, the protruding element is a diamond shape with glitters over it.

Optionally, the protruding element is a hallmark, dotted area, pattern and the like.

Optionally, the protruding element is configured on the lipstick arrangement in a slanted or an upright orientation. Specifically, the slanted orientation refers to when the protruding element is arranged on the lipstick arrangement at an angle with the horizontal axis of the lipstick arrangement. In an example, the protruding element may be arranged at an angle starting from 10, 15, 20, 25, 30, 35, 40, 45, 50, 60, 70 degrees up to 15, 20, 25, 30, 35, 40, 45, 50, 60, 70, 80 degrees with the horizontal axis of the lipstick arrangement. Moreover, the upright orientation refers to when the protruding element is arranged perpendicular to the horizontal axis (namely, along the vertical axis) of the lipstick arrangement.

Optionally, the first part and the second part are substantially equal in size and the protruding element is positioned therebetween; by "substantially equal" is meant in a range of 80% to 120%, more optionally 90% to 110%. More optionally, the first part is longer than the second part and the protruding element is positioned below a midpoint of the casing. Alternatively, optionally, the first part is shorter than the second part and the protruding element is positioned above the midpoint of the casing.

The lipstick bullet has an elongate shape comprising the sloping top portion. The sloping top portion provides for an edgy and angular portion that is of benefit to the given user when applying the lipstick bullet onto corners and sides of lips of the given user. Moreover, the sloping top portion provides for a marker for the user for identifying a point on the lipstick bullet to apply it on the lips of the given user.

The sloping top portion of the lipstick bullet is configured to face away from the protruding element, when the lipstick bullet is unscrewed to a fully deployed position, namely protruding out of the first part of the casing. Such different angular position of the protruding element allows for a user support for holding the casing when the given user employs the lipstick arrangement for user beautification purposes. Specifically, when the sloping top portion of the lipstick bullet faces away from the protruding element, the user of the lipstick arrangement when applying lipstick may rest one of their fingers (such as a thumb or an index finger) on the protruding element to gain a better grip on the lipstick arrangement and facilitate a more uniform, smoother application of the lipstick.

Optionally, the sloping top portion of the lipstick bullet is configured to face in a radial direction that is in a range of 60 degrees to 180 degrees away from radial direction of the protruding element. In an example, the sloping top portion of the lipstick bullet is configured to face in a radial direction that is in a range from 60, 65, 75, 80, 85, 90, 95, 100, 110, 120, 130, 140, 150, 160 degrees up to 70, 75, 80, 85, 90, 95, 100, 110, 120, 130, 140, 150, 160, 170 180 degrees away from radial direction of the protruding element.

Optionally, the sloping top portion of the lipstick bullet is configured to face in a radial direction that is mutually opposite to a radial direction of the protruding element, relative to the aforesaid elongate axis. The sloping top portion faces the given user when the lipstick bullet is unscrewed completely from the first part, namely to deploy the lipstick bullet to a maximum extent. Additionally, the protruding element faces a direction that is opposite to the given user when the lipstick bullet is unscrewed completely.

More optionally, the lipstick bullet comprises a ridge that is configured to face substantially in the same angular direction as the protruding element. For example, when the lipstick bullet is fully deployed or partially deployed. The ridge ensures that the lipstick bullet has a shape that makes it suitable for defining the user's cupid bow (namely, an upper lip biological feature). More optionally, the ridge extends from 10% to 80% of an elongate length of the lipstick bullet. More preferably, the ridge extends in a range of 10% to 40% of the elongate length of the lipstick bullet. The length of the ridge allows the lipstick bullet to keep its shape, even after multiple swipes across the user's lips for user beautification purposes, for a much longer duration than for known types of lipstick bullets, that become flat and lose their shape after only a few user beautification sessions.

Optionally, the protruding element positions along the lipstick arrangement, so that the lipstick arrangement is more easily user accessed from its packaging carton during transport or when stored in a purse, a bag, and a backpack. The protruding element helps the given user to position angularly the lipstick arrangement while packaging and transportation thereof in a packaging carton. The lipstick arrangement is optionally packed based on a positioning of the protruding element in the packaging carton, for example for aesthetic effect as well as ensuring effective protection of the lipstick arrangement against impact damage. In an example, the lipstick arrangement is stored in a bag of the given user, so that the protruding element faces in an outward direction.

Optionally, the protruding element helps to provide an identification of the lipstick arrangement, when there is difficulty in visibility of the lipstick arrangement; when the protruding element is metallized, for example with a gold surface finish, the lipstick arrangement is readily discernible in amongst a collection of other user beautification products. In an example, a user with visual impairment may identify the lipstick arrangement and a correct way to use the lipstick bullet by touching and identifying the protruding element on the lipstick arrangement. In another example, the lipstick arrangement may be identified by a user in a situation where there is lack visibility by locating the protruding element on the lipstick arrangement. The protruding element provides a useful tactile spatial reference that renders the lipstick arrangement much easier to manipulate and use.

Optionally, the lipstick bullet has the sloping top portion at two opposite sides thereof. In other words, the lipstick bullet has two sloping top portions at opposite sides of the lipstick bullet. The protruding element optionally faces any one of the two sloping top portions.

As aforementioned, the lipstick arrangement comprises the protective covering configured to cover the first part of the casing. The protective covering covers, for example, a top open part of the first part that accommodates the lipstick bullet. Therefore, the protective covering covers the distal end of the lipstick bullet. Furthermore, the protective covering is manufactured from materials such as fiber materials, plastics materials, glass, metals or metal alloys and the like. In an example, the protective covering may have graphical designs formed over an external surface thereof, for example by way of moulded embossing, laser ablation or printing processes. Furthermore, the protective covering may have crystals to increase (namely, to assist user finger grip onto the protective covering) a contact friction of the external surface in surrounding areas around the protruding element and preferably all over the casing to make it easier for the given user to take off the protective covering and to enhance grip in holding the casing, as well as to increase an aesthetic appearance of the lipstick arrangement. The protective covering has dimensions (namely, dimensional size) such that it is able to cover a top of the first part, as aforementioned.

Optionally, the protective covering covers, when in operation, a whole of the first part of the casing. Alternatively, optionally, the protective covering covers in operation a partial area of the first part of the casing.

Optionally, the protective covering covers, when in operation, the first part as well as the second part.

Optionally, the protective covering has a dome-shaped top to provide enough room to accommodate the lipstick bullet in the first part when the lipstick bullet is retracted by using the aforesaid screw mechanism. Alternatively, the protective covering has a flat top. In an example, the top of the protective covering is a surface with curves thereon.

Optionally, the lipstick arrangement allows for opening the protective covering by pressing, pushing or moving the protruding element. However, optionally, the protruding element has a degree of flexibility and also has an inwardly protruding notch that engages with an outwardly projecting feature of the protective covering that allows for the protective covering to be snap-retained over the first part; such snap-retention of the protective covering onto the protruding element provides a reassuring "click" sound when the protective covering is pushed to cover the first part securely, and also provides a tactile response that the given user may find aesthetically pleasing and reassuring. Such snap-retention will be described in more detail later, with reference to FIG. 6.

Optionally, the protective covering comprises internal elongate facets for secure locking on the first part of the casing, the facets have an elongate orientation that is parallel to an elongate axis of the protective covering; optionally, the elongate facets are implemented in a helical or spiral form; the elongate facets abut onto an external outwardly-facing surface of the first part of the casing, when the protective covering is installed over the first part of the casing, to provide protection for the retracted lipstick bullet. The facets are included to reduce a risk of the protective covering becoming stuck to the first part of the casing, and therefore difficult for the given user to remove, when smears of the lipstick bullet onto the external outwardly-facing surface of the first part of the casing. Thus, the facets assist to provide or more reliable and consistent operation of the lipstick arrangement, even when the lipstick bullet has migrated by way of smears onto various surfaces of the lipstick arrangement.

Optionally, the protective covering is attached to the first part and covers the top of the first part, wherein the top of the first part allows for a path for screwing and unscrewing the lipstick bullet in and out of the first part.

Alternatively, optionally, the protective covering is removed from a top of the first part. Furthermore, removing the protective covering from top of the first part allows for unscrewing the lipstick bullet out of the first part.

More optionally, the first part of the casing includes a locking mechanism to prevent covering of the first part of the casing by the protective covering, when the lipstick bullet protrudes from the first part of the casing. The locking mechanism includes an indentation on the first part that moves in an outward direction when the lipstick bullet is unscrewed and in an inward direction when the lipstick is screwed. Furthermore, the indentation of the locking mechanism extends completely within a socket positioned on the first part. In other words, the locking mechanism is visible only when the lipstick bullet is unscrewed and is deployed out from the first part. The locking mechanism is not visible when the lipstick bullet is retracted and encased within the first part. Beneficially, the locking mechanism creates a hindrance in a path of the protective covering when applied at least partially over the first part, when the lipstick bullet is not completely retracted within the first part. Therefore, the locking mechanism allows for the protective covering to cover the first part only when the lipstick bullet is completely retracted and accommodated within the first part.

Optionally, the lipstick arrangement comprises a surface coating on the casing and the protective covering for better grip, as aforementioned. The casing and the protective covering may have the coating having an anti-slip texture that provides a better grip to fingers of the user holding the lipstick arrangement. In an example, the coating on the casing and the protective covering may be of rubber, polymer and the like.

More optionally, the protective covering has a blocking element at a top internal portion thereof. The blocking element is designed so that it does not damage the lipstick bullet in case it comes in contact with the lipstick bullet. At an instance, when the lipstick bullet is half screwed and the user makes an attempt to put on the locking mechanism, the blocking element prevents the lipstick bullet from becoming damaged and creates a blockage. Therefore, the blockage created by the blocking element indicates to the user that the lipstick bullet is half screwed.

Optionally, the first part has a safety band running at an internal area of top of the first part. In an example, the safety band may have a bright color and may have glitters to make it more visible to the user. The complete visibility of the safety band assists to ensure in operation that the lipstick bullet is completely screwed, namely retracted. Alternatively, the invisibility or partial visibility of the safety band indicates that the lipstick bullet is unscrewed or partially screwed.

More optionally, the lipstick arrangement is configured to have the lipstick bullet in small size for a purpose of testing by the user, for example by way of an item for sales promotion.

Optionally, the lipstick arrangement has a height in a range of 5 centimeters (cm) to 15 centimeters (5 cm). Furthermore, the lipstick arrangement is conveniently in a form of an elongate circular-cross-section stick has a radius in a range of 0.5 centimeter (cm) to 2.0 centimeters (cm). Alternatively, the lipstick arrangement in form of a rectangular stick has an elongate length in a range of 1 centimeter (cm) to 2.5 centimeters (cm). Moreover, the lipstick arrangement is implemented in a form of a rectangular-cross-section stick that has a lateral breadth in a range of 1 centimeter (cm) to 2.5 centimeters (cm).

Optionally, the top part and the second part have substantially similar or different dimensions depending upon a design of the lipstick arrangement. For example, by "substantially" is meant in a range of 80% to 120%, wherein 100% corresponds to mutually identical.

In an exemplary implementation, the lipstick arrangement may have a shape of an elongate circular-cross-section stick. For example, the casing of the lipstick arrangement may have a height of 73.50 mm with a radius of 21 mm. Also, the walls of the lipstick arrangement may have a thickness of 0.50 mm. Furthermore, the first part of the lipstick arrangement may have a height of 48.50 mm and the second part of the lipstick arrangement may have a height of 25 mm. Additionally, a radius of the first part and the second part may be equal. Yet additionally, the protective covering may have a height of 49.77 mm. The first part and the second part of the lipstick arrangement may have a mechanism, for example a screw mechanism, that pushes the carrier in an axially outward direction when any one of: the first part and the second part are rotated relative to one another, for example the first part is rotated in a clockwise direction relative to the second part. Additionally, the first part and the second part may have a mechanism that pulls, namely retracts, the carrier back within the first part when the first part is rotated relative to the second part, for example the first part is rotated in an anticlockwise direction relative to the second part.

DETAILED DESCRIPTION OF THE DRAWINGS

Figure 2:
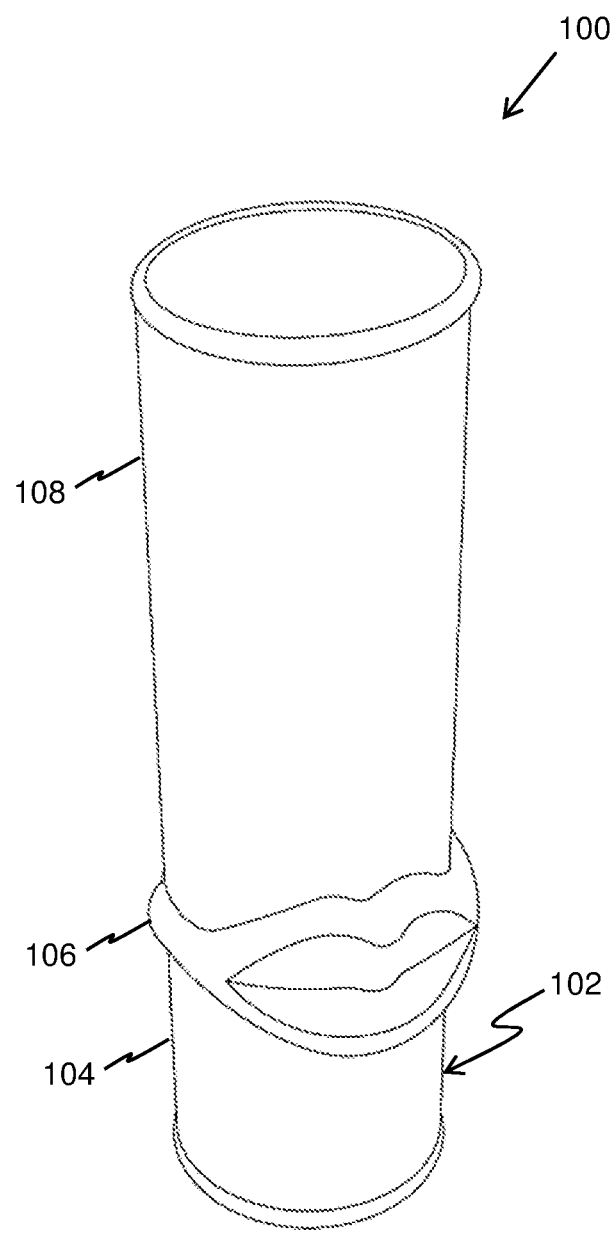
FIG. 2 is an illustration of a perspective view of the lipstick arrangement of FIG. 1 in the closed configuration, in accordance with an embodiment of the present disclosure.

Referring to FIGS. 1 and 2, there is illustrated a front view and a perspective view respectively, of a lipstick arrangement 100 in a closed configuration, in accordance with an embodiment of the present disclosure. The lipstick arrangement 100 comprises a casing 102. The casing 102 comprises a first part (shown in FIG. 3) and a second part 104; the first part and the second part are mutually coupled, for example susceptible to being rotated relative to one another about an elongate axis of the lipstick arrangement 100. The casing further comprises a protruding element 106 attached to the second part 104; optionally, at least a portion of the protruding element 106 is susceptible to flex in operation relative to the second part 104 and/or the first part, to provide for snap-fit retention of a protective covering 108; the protective covering 108 is configured to cover the first part of the casing 102.

Figure 3:
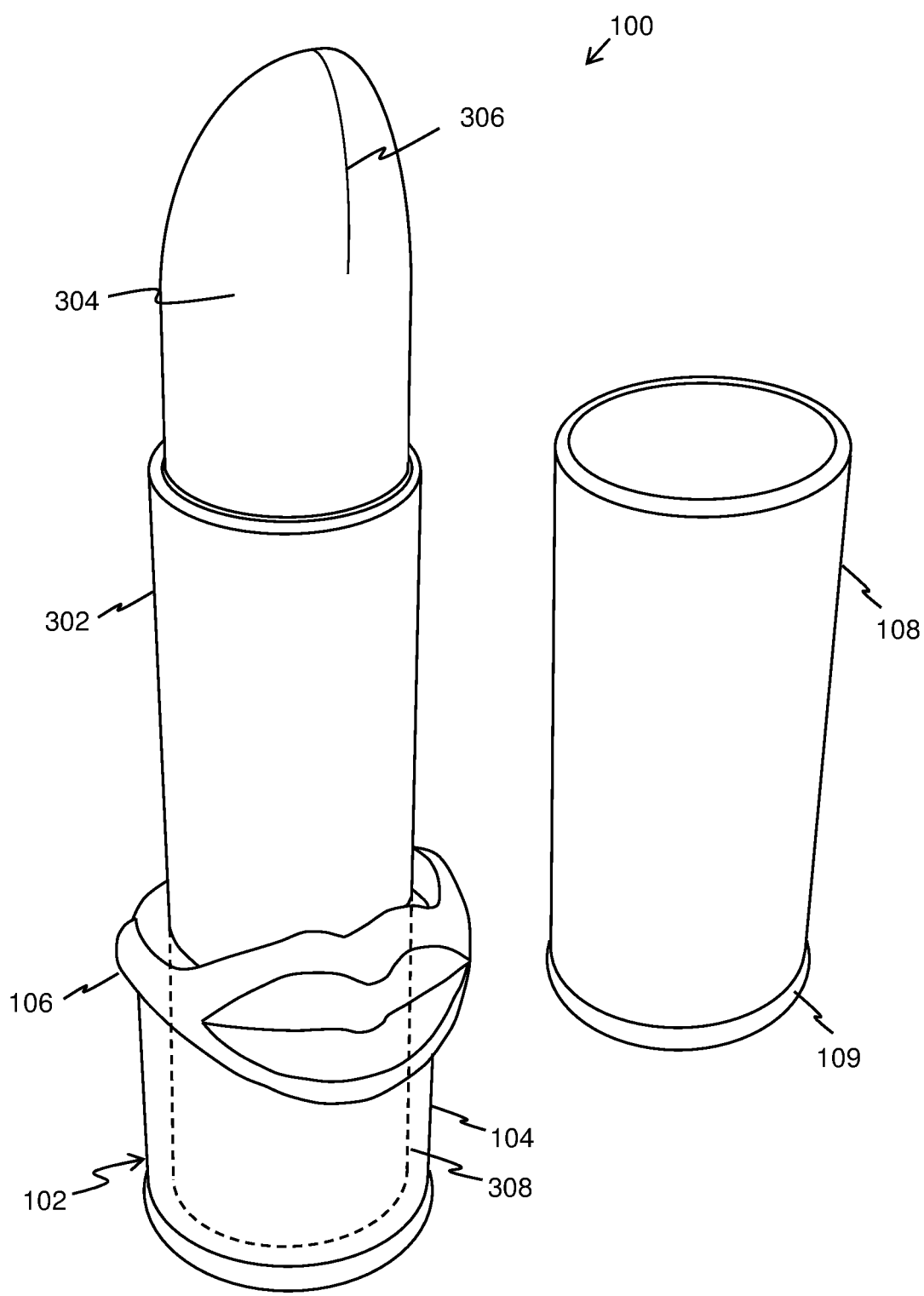
FIG. 3 is an illustration of a perspective view of the lipstick arrangement of FIG. 1 in an open configuration, in accordance with an embodiment of the present disclosure.

Referring to FIG. 3, there is illustrated a perspective view of the lipstick arrangement 100 in an open configuration, in accordance with an embodiment of the present disclosure. As shown, the lipstick arrangement comprises the casing 102. The casing 102 comprises a first part 302 comprising a carrier 308 therein. A lipstick bullet 304 is mounted onto the carrier 308. The casing 102 further comprises the second part 104. The first part 302 and the second part 104 are configured to be mutually rotatable, wherein the carrier 308 is operatively coupled to the first part 302 and the second part 104 and is configured to move in an axial direction along the aforesaid elongate axis in response to a rotation of at least one of the first part 302 relative to the second part 104. The lipstick arrangement 100 comprises the protective covering 108 configured to cover the first part 302 of the casing 102.

Figure 4:
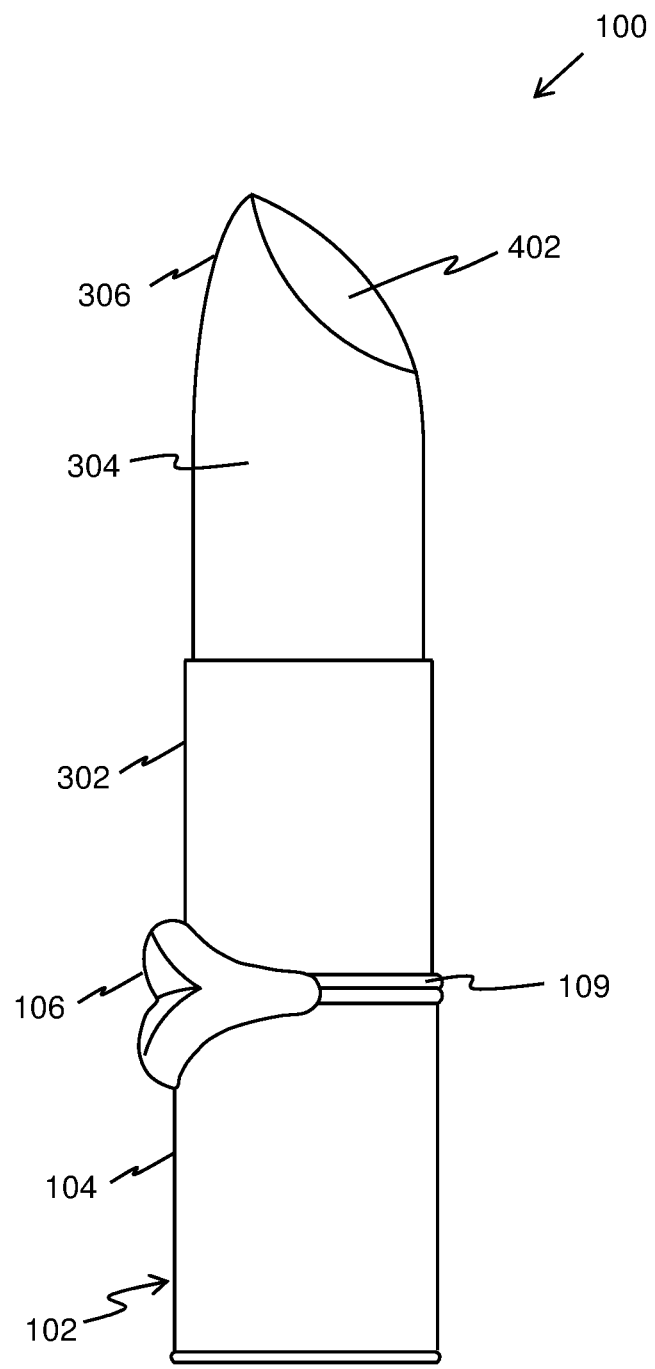
FIG. 4 is an illustration of a side view of the casing, in accordance with an embodiment of the present disclosure.

Referring next to FIG. 4, there is illustrated a side view of the casing 102, in accordance with an embodiment of the present disclosure. The casing 102 comprises the first part 302 comprising a carrier 308 therein, wherein the lipstick bullet 304 is mounted on the carrier 308, as aforementioned. The lipstick bullet 304 has an elongate shape comprising a sloping top portion 402 and a ridge 306. As shown, the sloping top portion 402 of the lipstick bullet 304 is configured to face in a direction that is substantially mutually opposite to a direction in which the protruding element 106 faces. The ridge 306 is configured to face in the same direction as the protruding element 106. The ridge 306 is configured to be substantially aligned with the middle of the protruding element 106. The middle of the protruding element 106 is a central point equidistant from either starting point of the protruding element 106 along the circumference of the casing 102.

Figure 5:
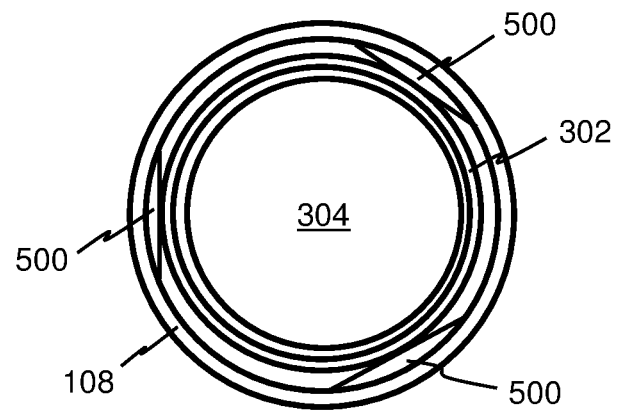
FIG. 5 is an illustration of an abutment of a protective covering of the lipstick arrangement, onto a first part of a casing of the lipstick arrangement, wherein the abutment is provided by employing a plurality of elongate facets formed into an inside facing surface of the protective covering (for example, three or four such elongate facets are beneficially employed as illustrated)
Figure 5:
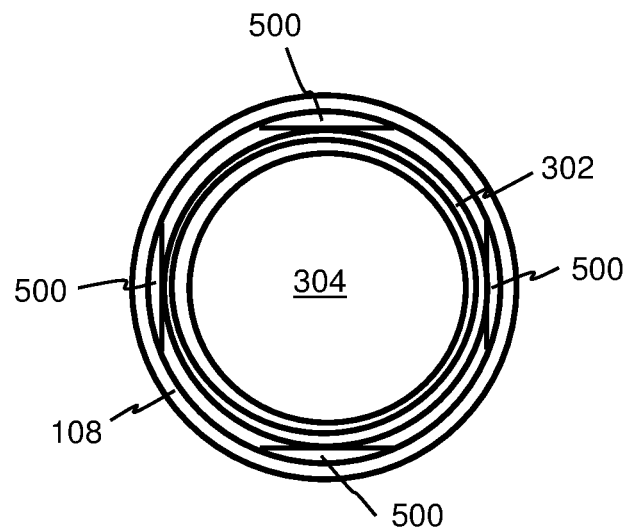

Referring next to FIG. 5, there is illustrated cross-section views of the first part 302 and its associated lipstick bullet 304; the carrier 308. There is also shown the protective covering 108 whose inside surface has formed thereon to a plurality of elongate facets 500 that abut an outwardly-facing side surface of the first part 302. For example, there are optionally, three or four facets 500 provided, as illustrated, although more than four facets 500 are optionally employed. The facets 500 potentially avoid the protective covering 108 becoming stuck onto the outwardly-facing side surface of the first part 302 in an event that traces of the lipstick bullet 304 become inadvertently smeared onto the outwardly-facing side surface of the first part 302. As aforementioned, the facets 500 have an elongate orientation that is substantially parallel to the elongate axis of the lipstick arrangement 100 when the protective covering 108 is placed over the first part 302. Optionally, the facets 500 are formed in a spiral or helical manner onto the inwardly facing surface of the protective covering 108.

Figure 6:
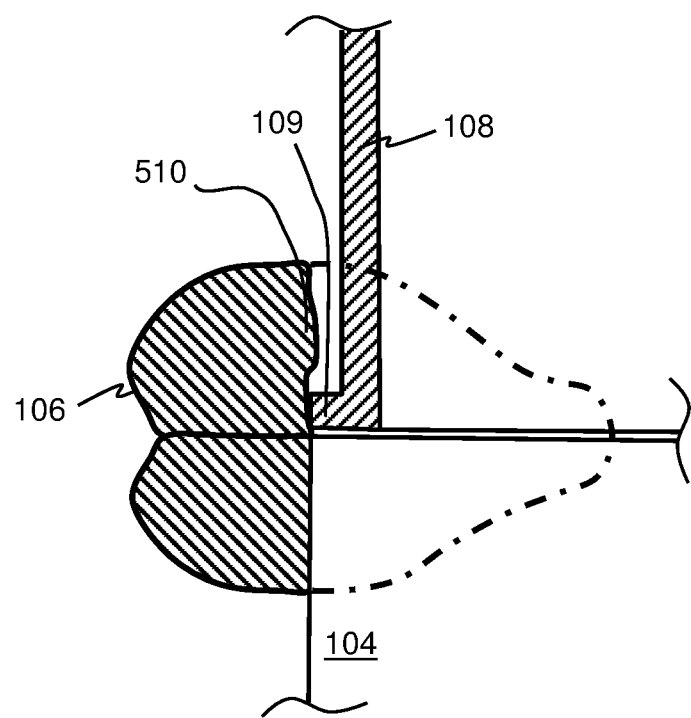
FIG. 6 is an illustration of a snap-fit retention of the protective covering illustrated in FIG. 5 of the lipstick arrangement onto a protruding element of a casing of the lipstick arrangement.

Referring next to FIG. 6, there is illustrated in cross-section a portion of the lipstick arrangement 100 that provides for a tactile snap-retention of the protective covering 108 onto the first part 302 of the casing 102. The protective covering 108 includes a radially protruding lip 109 at an end thereof that abuts onto the protruding element 106. The radially protruding lip 109, in operation, contacts onto an inwardly-facing projection 510 for providing a tactile passing of the protective covering 108 relatively to the first part 302. The tactile passing provides the given user with a tactile impulse as well as an acoustic "click", which is aesthetically pleasing, as well as providing confirmation of the protective covering 108 being completely and firmly abutted to the casing to ensure protection of the lipstick bullet 304.

Figure 7:
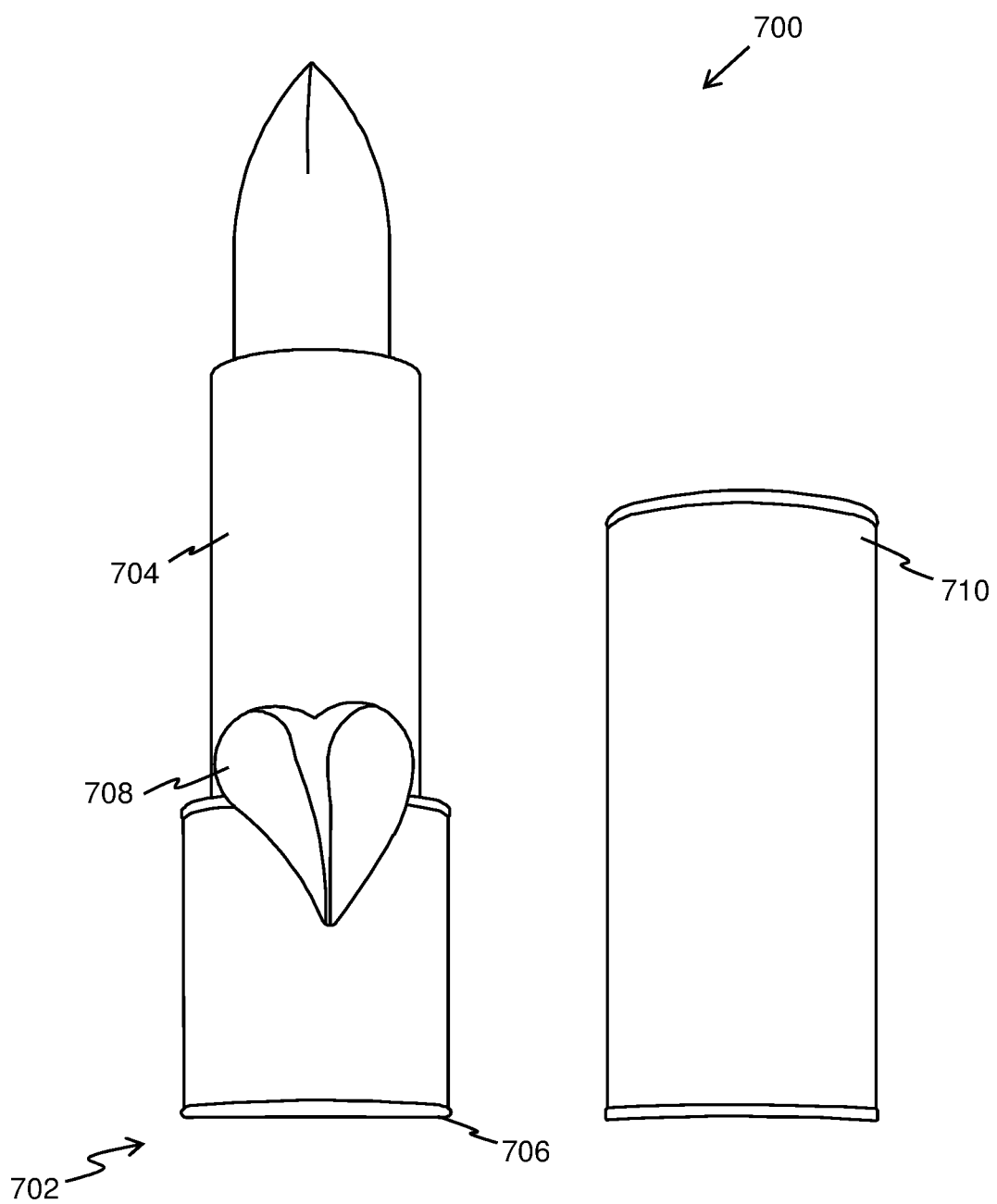
FIGS. 7 and 8 are illustrations of a front view of a lipstick arrangement in an open configuration, in accordance with various implementations of the present disclosure.
Figure 8:
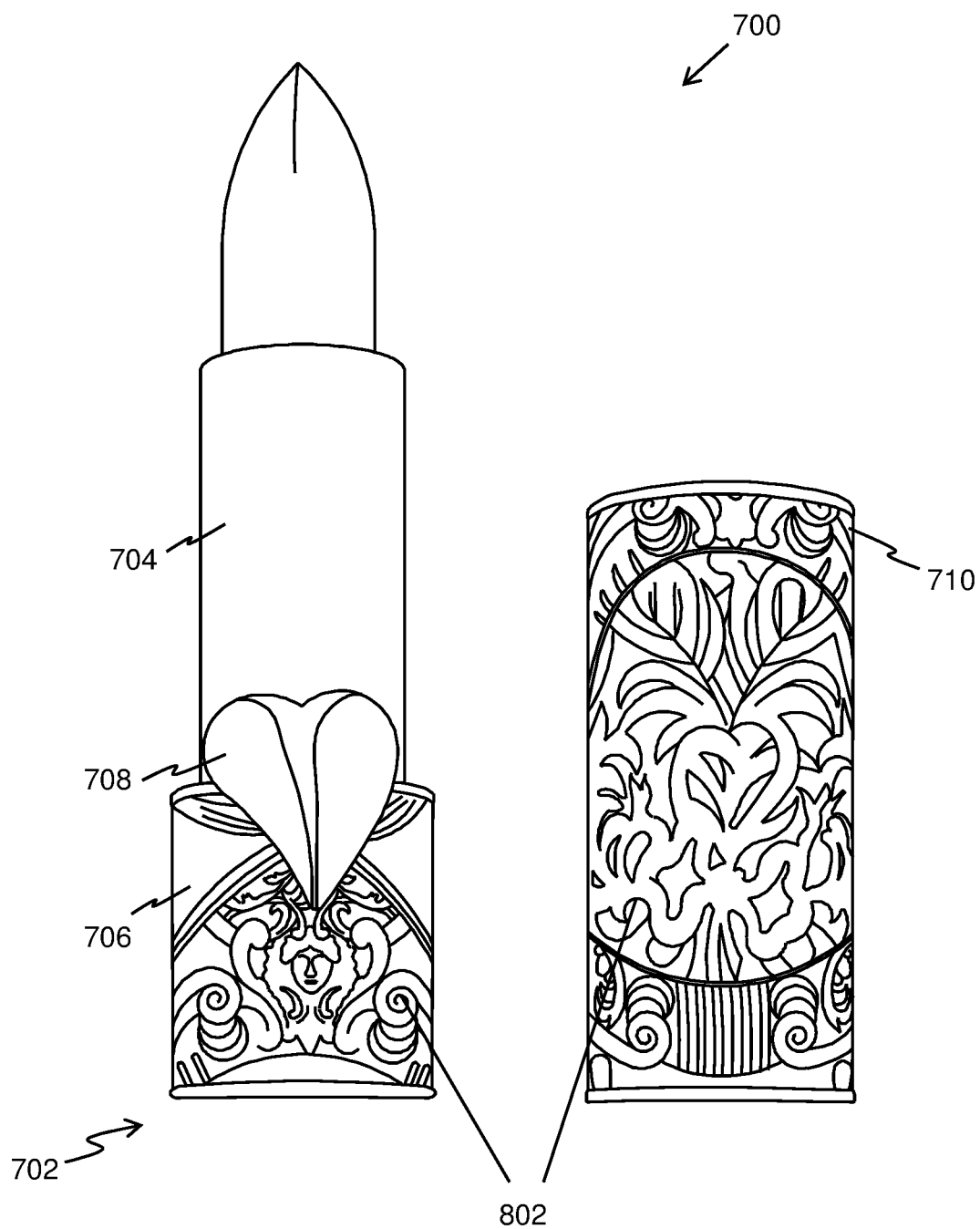

Referring to FIGS. 7 and 8, there are illustrated a front view of a lipstick arrangement 700 in an open configuration, in accordance with an implementation of the present disclosure. The lipstick arrangement 700 comprises a casing 702. The casing 702 comprises a first part 704 and a second part 706. The casing 702 further comprises a protruding element 708, implemented as a crooked heart structure, attached to the second part 706. At least a portion of the protruding element 708 is susceptible to flex in operation relative to the second part 706 and/or the first part 704, to provide for snap-fit retention of a protective covering 710. The protective covering 710 is configured to cover the first part 704 of the casing 702. As shown in FIG. 8, the outer surfaces of the first part 704 of the casing 702 and the protective covering 710 are provided with a finish, implemented as a grip-enhancing coating having an anti-slip texture, onto which an artwork 802, implemented as printed graphical images or embossing, is provided. The outer surfaces of the second part 706 of the casing 702 is plain and not provided with printed graphical images or embossing.

Figure 9:
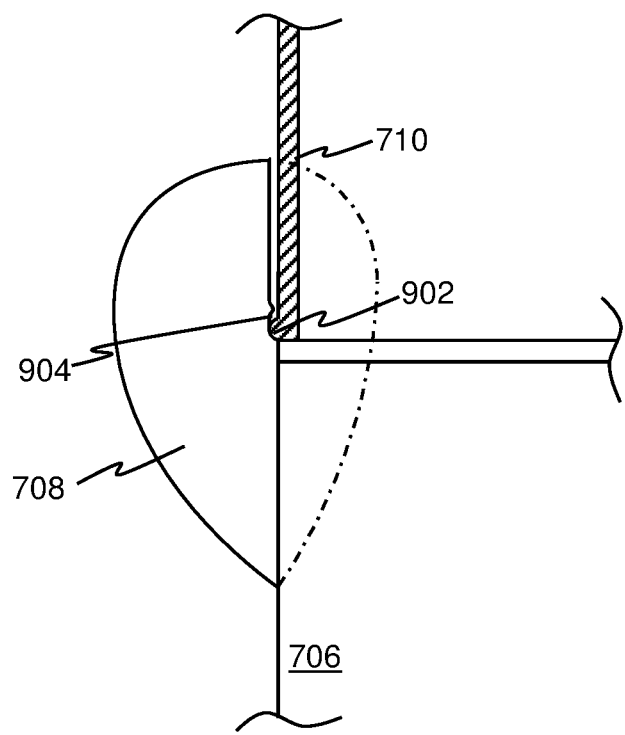
FIG. 9 is an illustration of a snap-fit retention of the protective covering of the lipstick arrangement onto a protruding element of a casing of the lipstick arrangement.

Referring to FIG. 9, there is illustrated in cross-section a portion of the lipstick arrangement 700 that provides for a tactile snap-retention of the protective covering 710 onto the first part 704 of the casing 702. The protective covering 710 includes a radially protruding element 902 at an end thereof that abuts onto the protruding element 708. The radially protruding element 902, in operation, contacts onto an inwardly-facing projection 904 for providing a tactile passing of the protective covering 710 relatively to the first part 704 of the of the casing 702 The tactile passing provides the given user with a tactile impulse as well as an acoustic "click", which is aesthetically pleasing, as well as providing confirmation of the protective covering 710 being completely and firmly abutted to the casing to ensure protection of the lipstick bullet.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A lipstick arrangement comprising:
   a casing comprising:
      a first part, wherein
         a carrier is located at a bottom region of the first part, wherein
            a lipstick bullet is mounted on the carrier and has an elongate shape comprising a sloping top portion;
         a second part, wherein
            the carrier is operatively coupled to the first part and the second part, and
            wherein the carrier is configured to move in an axial direction relative to the second part in response to the first part being rotated relative to the second part; and
         a protruding element attached to the second part; and
      a protective covering that is configured to cover the first part of the casing when applied to the casing, wherein
         an internal surface of the protective covering comprises a plurality of facets configured to abut on the first part of the casing,
         a first facet of the plurality of facets is separated from a second facet of the plurality of facets on the internal surface of the protective covering, and
         the sloping top portion of the lipstick bullet is configured to face away from the protruding element when the lipstick bullet is unscrewed to a fully deployed position,
         wherein the protruding element provides for flexural retention over an outwardly projecting feature of the protective covering, for snap fit retention of the protective covering onto the protruding element.

2. The lipstick arrangement of claim 1, wherein the sloping top portion of the lipstick bullet is configured to face in direction that is in a range of 60 degrees to 180 degrees away from direction of the protruding element.

3. The lipstick arrangement of claim 1, wherein the sloping top portion of the lipstick bullet is configured to face in direction that is mutually opposite to direction of the protruding element.

4. The lipstick arrangement of claim 1, wherein the lipstick bullet comprises a ridge configured to face in a same direction as the protruding element.

5. The lipstick arrangement of claim 4, wherein the ridge extends from 10% to 80% of an elongate length of the lipstick bullet.

6. The lipstick arrangement of claim 1, wherein the lipstick arrangement comprises a grip-enhancing coating having an anti-slip texture on the casing and the protective covering, that is configured to provide a better grip to fingers of a user holding the lipstick arrangement.

7. The lipstick arrangement of claim 1, wherein the protruding element is any one of: a lip structure, a crown structure, a heart structure, a diamond structure, or a combination thereof.

8. The lipstick arrangement of claim 1, wherein the protruding element is arranged at an angle with a horizontal axis of the lipstick arrangement, wherein the angle of the protruding element with the horizontal axis of the lipstick arrangement is in a range of 10 degrees to 90 degrees.

9. The lipstick arrangement of claim 1, wherein the protruding element is configured to position the lipstick arrangement in any one of a packaging carton, a purse, a bag, or a backpack in a way that prevents damage to the corresponding any one of the packaging carton, the purse, the bag, or the backpack.

10. The lipstick arrangement of claim 1, wherein the lipstick bullet-mounted on the carrier is actuated along an elongate axis of the lipstick arrangement, in response to the first part being rotated relative to the second part, for deploying and retracting the lipstick bullet from the casing.

11. The lipstick arrangement of claim 1, wherein the lipstick bullet is a cosmetic composition comprising at least one of a non-ionic alkyl phosphate, a base, a humectant, water, a structuring agent, oil, a pigment, or a glitter.

12. The lipstick bullet when used in the lipstick arrangement of claim 11, wherein the lipstick bullet is a lip color, lip balm, or lip gloss.

13. The lipstick bullet when used in the lipstick arrangement of claim 11, wherein the lipstick bullet gives a glossy, lustrous, matte, or shimmery effect, when applied to lips of a user.

14. The lipstick arrangement of claim 1, wherein the protective covering is retained onto the protruding element in a snap-fit retention, when the protective covering is applied to cover the first part.

* * * * *